United States Patent
Klausz et al.

(10) Patent No.: US 9,898,840 B2
(45) Date of Patent: Feb. 20, 2018

(54) SYSTEMS AND METHODS FOR CONTINUOUS MOTION BREAST TOMOSYNTHESIS

(71) Applicant: General Electric Company, Schenectady, NY (US)

(72) Inventors: Remy Andre Klausz, Yvelines (FR); John Eric Tkaczyk, Niskayuna, NY (US); Henri Souchay, Versailles (FR); Scott Stephen Zelakiewicz, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 776 days.

(21) Appl. No.: 14/278,353

(22) Filed: May 15, 2014

(65) Prior Publication Data

US 2015/0332485 A1  Nov. 19, 2015

(51) Int. Cl.
*G06T 11/00* (2006.01)
*A61B 6/00* (2006.01)
(Continued)

(52) U.S. Cl.
CPC .......... *G06T 11/006* (2013.01); *A61B 6/025* (2013.01); *A61B 6/486* (2013.01); *A61B 6/502* (2013.01);
(Continued)

(58) Field of Classification Search
CPC ......... A61B 6/025; A61B 6/486; A61B 6/502; A61B 6/5205; A61B 6/547; G06T 11/005;
(Continued)

(56) References Cited

U.S. PATENT DOCUMENTS

| | | |
|---|---|---|
| 4,494,141 A | 1/1985 | Altekruse |
| 4,504,909 A | 3/1985 | Acharya et al. |
| | (Continued) | |

FOREIGN PATENT DOCUMENTS

| | | |
|---|---|---|
| CN | 102867294 A | 1/2013 |
| EP | 2107888 A2 | 10/2009 |
| WO | 2008/085577 A2 | 7/2008 |

OTHER PUBLICATIONS

Bleuet, Reconstruction 3D par tomosynthèse généralisée: application à l'imagerie médicale par rayons X, 2002, Doctoral thesis, INSA Lyon, 150 pages.*

(Continued)

*Primary Examiner* — Glen Kao
(74) *Attorney, Agent, or Firm* — Pabitra K. Chakrabarti

(57) ABSTRACT

A method of continuous motion digital tomosynthesis includes exposing an object to a programed intensity x-ray beam as an x-ray source travels a pre-determined path, accumulating a signal charge from the x-ray beam, recording the accumulated signal charge into a digital frame image representing raw baseline data, acquiring information on the source's and the detector's position when the recording occurs, compressing the raw baseline data into compressed views, where each respective compressed view is formed by combining the raw data readouts of the respective compressed view, and reconstructing a volumetric breast image by processing each respective compressed view with a reconstruction process function that incorporates the acquired position information and a spatial sampling corresponding to the compressed views. A system configured to implement the method and a computer-readable medium are also disclosed.

18 Claims, 4 Drawing Sheets

(51) Int. Cl.
  *A61B 6/02*    (2006.01)
  *G06T 7/00*    (2017.01)
  *G06T 7/73*    (2017.01)
(52) U.S. Cl.
  CPC ............ *A61B 6/5205* (2013.01); *A61B 6/547* (2013.01); *G06T 7/0012* (2013.01); *G06T 7/74* (2017.01); *G06T 11/005* (2013.01); *G06T 2207/10081* (2013.01); *G06T 2207/10116* (2013.01); *G06T 2207/20112* (2013.01); *G06T 2207/30068* (2013.01); *G06T 2211/421* (2013.01); *G06T 2211/424* (2013.01); *G06T 2211/436* (2013.01)
(58) Field of Classification Search
  CPC ......... G06T 11/006; G06T 2207/10081; G06T 2207/10116; G06T 2207/20112; G06T 2207/30068; G06T 2211/421; G06T 2211/424; G06T 2211/436; G06T 7/0012; G06T 7/0044
  See application file for complete search history.

(56) References Cited

U.S. PATENT DOCUMENTS

| | | | |
|---|---|---|---|
| 4,554,633 | A | 11/1985 | Glover et al. |
| 5,309,356 | A | 5/1994 | Nishide et al. |
| 5,594,769 | A | 1/1997 | Pellegrino et al. |
| 5,999,836 | A | 12/1999 | Nelson et al. |
| 6,754,298 | B2 | 6/2004 | Fessler |
| 6,801,594 | B1 | 10/2004 | Ali et al. |
| 7,212,606 | B2 | 5/2007 | Souchay et al. |
| 8,229,199 | B2 | 7/2012 | Chen et al. |
| 8,246,543 | B2 | 8/2012 | Johnson et al. |
| 8,284,894 | B2 | 10/2012 | Poorter |
| 8,340,388 | B2 | 12/2012 | Rosenstengel |
| 2003/0161443 | A1* | 8/2003 | Xiao et al. ............ G06T 11/006 378/210 |
| 2005/0135558 | A1* | 6/2005 | Claus ................. A61B 6/02 378/42 |
| 2007/0003132 | A1* | 1/2007 | Proksa ................. G06T 11/006 382/154 |
| 2008/0095420 | A1 | 4/2008 | Ohyu et al. |
| 2009/0022264 | A1 | 1/2009 | Zhou et al. |
| 2010/0128958 | A1 | 5/2010 | Chen et al. |
| 2010/0284596 | A1 | 11/2010 | Miao et al. |
| 2010/0303202 | A1 | 12/2010 | Ren et al. |
| 2012/0033868 | A1* | 2/2012 | Ren ........................ A61B 6/025 382/131 |
| 2012/0140878 | A1 | 6/2012 | Souchay |
| 2012/0224664 | A1 | 9/2012 | Maack |

OTHER PUBLICATIONS

Douyon, An Investigation into the Design of an Image Reconstruction Algorithm for Continuous Wave Tomosynthesis, Jun. 2013, Massachusetts Institute of Technology, Department of Electrical Engineering and Computer Science, Masters Thesis, 79 pages.*

Ren et al., Automatic patient motion detection in digital breast tomosynthesis, 2011, SPIE vol. 7961, pp. 5F-1 to 5F-12.*

Lyuboshenko, Igor et al., "Stable Signal and Image Reconstruction from Noisy Fourier Transform Phase", IEEE Transactions on Signal Processing, vol. 47, No. 1, Jan. 1999, (pp. 244-250, 7 total pages).

Zhou, Zhongxing et al., "Application of Fourier-wavelet regularized deconvolution for improving image quality of free space propagation x-ray phase contrast imaging.", Phys Med Biol., vol. 57, Issue 22, (2012), (pp. 7459-7579, 21 pages total).

PCT Search Report & Written Opinion issued in connection with corresponding PCT Application No. PCT/US2015/030672 dated Sep. 15, 2015.

* cited by examiner

| VALUE | UNITS | PARAMETER |
|---|---|---|
| 239.4 | MM | X SIZE OF DETECTOR (PERPENDICULAR TO CHEST WALL SIDE) |
| 306.2 | MM | Y SIZE OF DETECTOR ( ALONG CHEST WALL ) |
| 0.1 | MM | PIXEL WIDTH ( SQUARE PIXEL) |
| 2394 | # | NUMBER PIXELS ALONG X |
| 3062 | # | NUMBER PIXELS ALONG Y |
| 7,330,428 | # | NUMBER PIXELS IN DETECTOR AREA |
| 2 | SEC | SCAN TIME = X-RAY EXPOSURE & ALL VIEWS ACQUIRED |
| 200 | # | NUMBER OF VIEWS IN SCAN |
| 0.01 | SEC | INTEGRATION PERIOD |
| 14 | BITS | BIT DEPTH THAT ENCODES PIXEL GRAY-LEVEL VALUE |
| 102,625,992 | BITS | NUMBER OF BITS FOR ONE VIEW |
| 10.3 | GBITS/SEC | GIGA-BIT RATE |
| 20.5 | GBITS | TOTAL NUMBER OF BITS IN SCAN |

FIG. 3

SYSTEMS AND METHODS FOR CONTINUOUS MOTION BREAST TOMOSYNTHESIS

BACKGROUND

Digital breast tomosynthesis (DBT) is an imaging technique that allows a volumetric reconstruction of the whole breast from a finite number of projections obtained by different x-ray tube angles. DBT is an important tool used for screening and diagnostic mammography. This technique involves taking a series of x-ray images (projections) with the x-ray tube (also called the x-ray source) at different positions while the detector and breast are either relatively stationary or in relative motion. In conventional DBT the x-ray tube makes an arc, during which a series of images is acquired. Alternately, the x-ray tube can move along a linear path as is practiced today for a chest tomography, a related 3D imaging method. In another approach, the tube remains stationary and the detector is moved along a predetermined path. During the motion of the tube, a static or dynamic collimator stationed at the tube exit will direct the x-ray field so as to illuminate only the area of the detector. The acquired data is processed by a computer, where a reconstruction algorithm combines the projections to obtain sectional views of the breast.

Current systems use either a step-and-shoot configuration, where the tube (or detector) is stationary during x-ray exposure, or a continuous motion configuration, where the tube (or detector) is constantly moving but the x-rays are pulsed during the motion. The number of x-ray exposure cycles corresponds to the number of stationary positions or to the number of pulses respectively. During the time between each cycle, the X-ray intensity is zero so as to allow the system to move to the next angle location. In both these cases the tube is not run at full duty cycle, being off at least long enough to read out the detector and to move system components into the next angle position.

In step-and-shoot geometries there is no motion blur due to tube motion but the overall exam time is long. This is due to the time lag expended waiting for the moving component to accelerate from rest at the current position, come close to a new position, decelerate to rest, stop long enough for any vibrations to settle, and then perform the x-ray exposure before moving to the next position. The need to quickly perform an exam also leads to the support structure (gantry) used to move the tube to be made sufficiently strong and rigid to support the torque during acceleration and minimize vibrations. Powerful motors are needed to move the tube quickly between positions. Both of these increase the cost of the overall system.

In continuous motion systems with a pulsed x-ray tube there is substantial image blurring that occurs because a single detector frame is acquired while the tube (or detector) is moving during the x-ray exposure. To minimize this blurring one option is to increase the tube power and pulse with shorter exposure times. Higher power tubes can cost more and weigh more and release more heat into the system. The higher weight leads to additional system cost since larger motors and more rigid gantries are needed.

BRIEF DESCRIPTION OF THE DRAWINGS

FIG. 3 depicts in tabular form a representative calculation of the amount of data acquired during a scan in accordance with some embodiments.

DETAILED DESCRIPTION

In accordance with some embodiments, systems and methods provide a tomosynthesis system that includes an x-ray source (which at a minimum includes an electron beam and an anode target) which moves relative to the object to be imaged (e.g., a breast or chest) and the detector. In one implementation, the object and detector do not move relative to each other, though in other implementations they could. The x-ray source follows a path. For example, a line or arc, though other more complicated paths can be envisioned. The moving x-ray source generates a sequence of x-ray emission cycles that are coordinated with the detector readout so as to generate a number of images distinct from the number of x-ray cycles. The instantaneous x-ray field intensity may or may not change over the range of motion. The programed intensity profile generates x-rays either continuously at constant amplitude with variable intensity, or pulsed along this path in order to effect the number of x-ray cycles possibly with zero intensity periods between cycles. As the instantaneous x-ray field transverses the object the field is attenuated. The transmitted, attenuated x-ray field is then detected by an x-ray detector.

Figure 1:
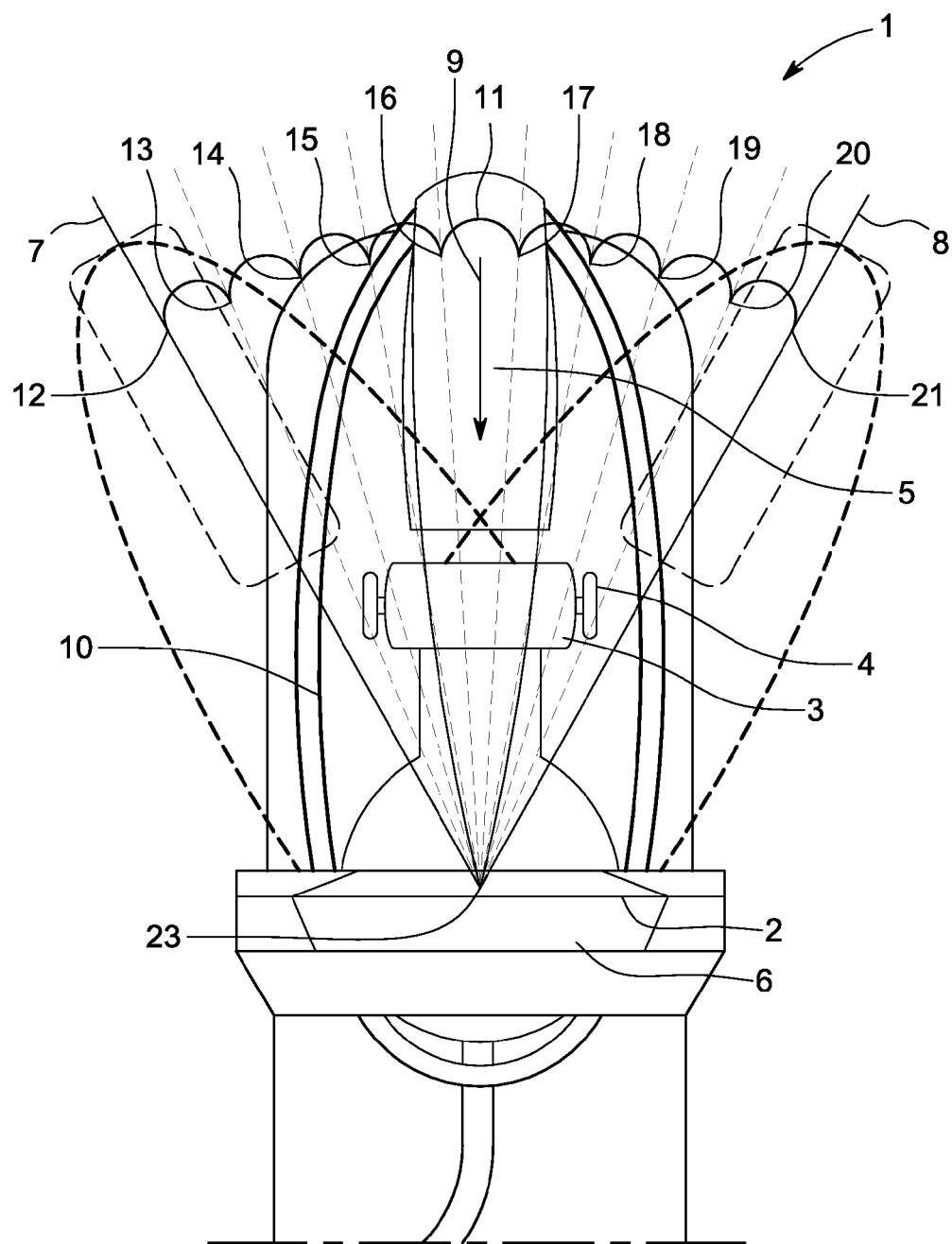
FIG. 1 depicts a radiographic projection tomography apparatus in accordance with some embodiments.

FIG. 1 depicts radiographic projection tomography apparatus 1 in accordance with some embodiments. Tomography apparatus 1 includes support 2 that can support an object to be subjected to tomography. In an embodiment, the tomography apparatus can be configured as a mammography apparatus wherein support 2 is a breast-holder support that supports a patient's breast. Nevertheless, any other type of tomography apparatus can be envisaged. Normally, the patient's breast is placed on the support and compressed by paddle 3 which can be maneuvered by an operator using for example handles 4. Tomography device 1 furthermore comprises a source of radiation, such as x-ray emitting tube 5 and detector 6. The detector is capable of detecting the rays after they have crossed the patient's breast. The detector 6 is placed beneath support 2. In practice, paddle 3 is made of an x-ray transparent material (e.g., plastic).

In accordance with one implementation, paddle 3, the patient's breast, support 2, and detector 6 are in fixed position, while the x-ray tube 5 may take up several positions in space relative to this assembly. In other implementations, the detector can travel in relation to the x-ray tube. In still other implementations, both the x-ray tube and the detector can move in a coordinated pattern relative to the patient's breast. Tomography device 1 includes a control processor which executes computer readable instructions to control the operation of device 1.

In particular, FIG. 1 shows distributed in reorientation between a first extreme position 7 and a second extreme position 8 that are, for example, symmetrical relative to each other relative to a bisecting direction 9. The positions are on the whole distributed on an arc of a circle. In the depicted implementation, arm 10 carries tube 5. There are other possible arrangements enabling the tube and/or the detector to shift in a plane or a sphere portion.

Tube 5 is provided with focal spot 11 that is the x-ray emitting focal spot. For a multiplicity of exposure positions, herein represented by ten positions numbered 12 to 21, the number of these positions being greater than or equal to 3, is related to arranging a mammography device whose tube is at a halt at the incidence (position) 7 and, after regular exploration, is also at a halt at the incidence (position) 8.

On the path, the positions are distributed, preferably evenly, even though, with the image reconstruction processing corrections, it would be possible to envisage a case where the positions 12 to 21 are not evenly distributed. In accordance with one embodiment, image data can be sampled at regular intervals along the arc of motion, i.e., in and around the positions 12 to 21.

As can be seen in FIG. 1, especially when the motion of the focal spot is cycloid, the exact path of the focal spot is not necessarily that of an arc of a circle or of a sphere portion but is inscribed in a circular or spherical ring portion. However, the cycloid motion could be made in a plane or on a sphere portion. In this case, the relative motion would be tangential to this plane or to the surface of this sphere.

In accordance with embodiments, the object of interest (e.g., a breast) is exposed to one or multiple x-rays shots that extend over multiple image readouts. Signal charge is accumulated in the detector pixels and periodic readout events read the charge from the pixels into a digital image frame. The detector can be operated in either a continuous readout (rolling shutter) mode, or in a charge storage mode (i.e., frame buffer mode, or global shutter). In the continuous readout mode all the pixels within a subset of all the pixels are read in parallel and different subsets of pixels are read sequentially. In the charge storage mode all the charge stored on the pixels are simultaneously transferred to storage capacitors before readout. Then readout of the storage capacitors occurs while the next frame is acquired by accumulation of signal charge onto the pixels.

Embodying systems are simpler, lower-cost DBT systems than conventional step-and-shoot DBT systems because of the simplified mechanical requirements needed to implement these embodiments. The improved duty cycle operation of the tube achieves a lower tube current to develop a total radiation dose required to obtain a quality image. Accordingly compared to a continuous motion system with a pulsed x-ray source exposing individual images, embodying systems have a reduced thermal requirement for the x-ray source resulting in lower cost. Embodying systems eliminate image blurring during the x-ray exposure by providing a sufficient multitude of detector reads so that object positions are projected to detector locations between adjacent views that are within one detector pixel pitch.

In accordance with embodiments, the detector can run in two possible modes. In one mode, a rolling shutter technique is implemented. Image data is collected by scanning across the detector frame either vertically or horizontally. Accordingly, not all parts of the image are recorded over exactly the same time interval. However, a time stamp, or other information as a function of time (e.g., angle, x position) providing information regarding the positions of the source and detector which allows identifying the location of the source at the time of image acquisition, is acquired at about the time the image portions are recorded. The rolling shutter can introduce predictable distortions, particularly for fast moving (relative to the data acquisition sampling) x-ray tube (or detector). For example, in one implementation a row of pixels on the detector can be read out in parallel. When completed, the next row is read-out, etc. After the last row is read out the first row is readout again. The acquired time stamps for the parts of the images read together are used for the purpose of 3D reconstruction.

In a second readout mode (frame buffer mode), all of the charges on individual pixels of the detector are transferred about simultaneously to a storage mechanism (e.g., the simplest being a storage capacitor attached to each pixel, or a memory device). The charge is then read from the storage capacitors while the next frame is acquired on the pixels. When the charges on the last of the storage capacitors are read, a new sequence begins where the new integrated charge on each pixel is again transferred to the storage capacitors.

In either detector readout method, each pixel will integrate signals from the x-ray field only for as long as it takes to readout the detector. Detectors that show fast frame rate capability include CMOS and amorphous-indium-gallium-zinc-oxide active pixel arrays. Fast digital methods for analog-to-digital conversion of signal charge are recently available from low cost and low power integrated electronics. Application specific integrated circuits (ASICs) and on-detector electronics can effectively read at frame rates of 30 to 1000 frames-per-sec. The short time for the signal charge integration can minimize any impact due to blurring, reduce the total exam time, and provide the maximal amount of projection data to use in a tomographic reconstruction.

In accordance with some embodiments, the high rate of projection data acquisition provides fine sampling of the relative angle position of the tube (or detector). Furthermore, the simplified gantry mechanics and overall fast time needed to complete an angular scan allows a wider angular range. The angular difference between first extreme position 7 and second extreme position 8 (FIG. 1) can be wider without introducing blur due to tube motion. The result of this maximal amount of projection data when used in tomographic reconstruction can create volumetric images with higher spatial resolution and better separation of tissues in regards to their distance from the detector.

Figure 2:
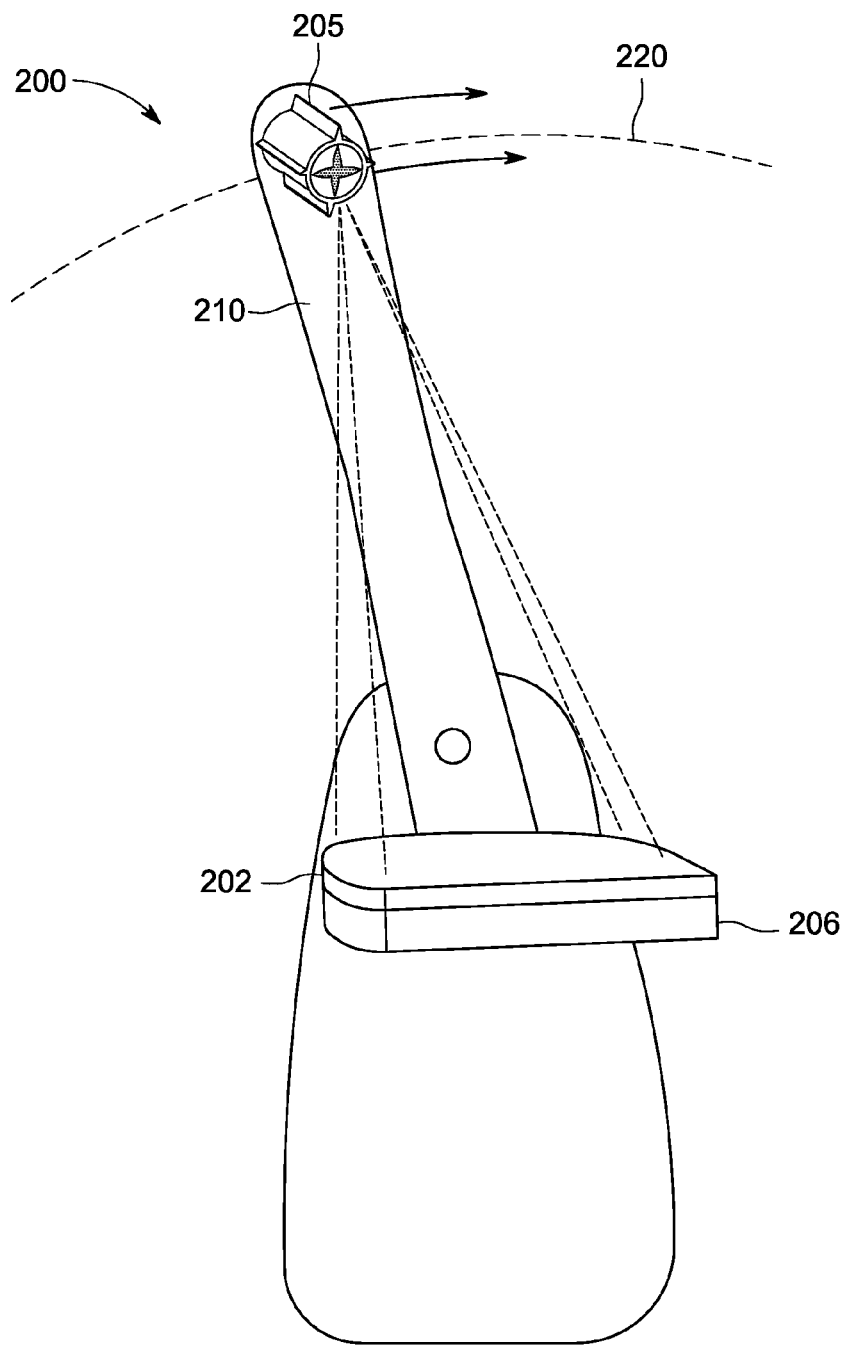
FIG. 2 depicts a portion of a radiographic projection tomography apparatus in accordance with some embodiments.

FIG. 2 depicts a portion of radiographic projection tomography apparatus 200 in accordance with some embodiments. In some implementations, tomography apparatus 200 can be incorporated into corresponding portions of radiographic projection tomography apparatus 1. In particular, tomography apparatus 200 includes support 202 that can support an object to be subjected to tomography. In an embodiment, the tomography apparatus can be configured as a mammography apparatus wherein support 202 is a breast-holder support to support a patient's breast. Tomography apparatus 200 includes a source of radiation, such as x-ray emitting tube 205 and detector 206. The detector is capable of detecting the rays after they have crossed the patient's breast. The detector is placed beneath support (breast-holder support) 202. Breast compression with paddle 3 (FIG. 1), possibly with less force or eliminated, would be possible because of the maximal projection data and fast scan time.

In accordance with one implementation, the patient's breast, support 202, and detector 206 are in fixed positions, while x-ray tube 205 may take up several positions in space relative to this assembly. In particular, the x-ray tube can travel along predetermined path 220 between a first extreme position and a second extreme position. The positions are on the whole distributed on an arc of a circle. In the depicted implementation, arm 210 carries tube 205. There are other possible arrangements enabling the tube and/or the detector to shift along a predetermined path in a plane or a spherical portion.

In accordance with embodiments, x-ray tube 205 is operated in a continuous wave (CW) mode with a programed X-ray intensity in conjunction with continuous, multiple detector reads as opposed to a pulse waveform with single readout per pulse. Operating the tube in CW lessens the maximum power requirements for the tube by maximizing the time during the source motion where x-rays are emitting. The detector can be sampled either in rolling shutter mode or frame buffer mode, as described above. As the detector is sampled, time stamp data is acquired. During image reconstruction, knowledge of the tube's position, rate of movement, travel path, and data time stamp can be used by a reconstruction algorithm to determine the real position of system components so as to produce a high resolution image of the breast, or object-under-study.

FIG. 3 depicts in tabular form (Table I) a representative calculation of the amount of data acquired during a scan in accordance with some embodiments. In accordance with embodiments, a significant quantity of data can be obtained during the scan. The calculation is based on detector parameters, scan time, frame rate, and data collection. As illustrated by Table I, a representative scan can acquire about 20.5 Gbits of data. Accordingly, data compression techniques can be implemented by the system to reduce storage requirements.

Figure 4A:
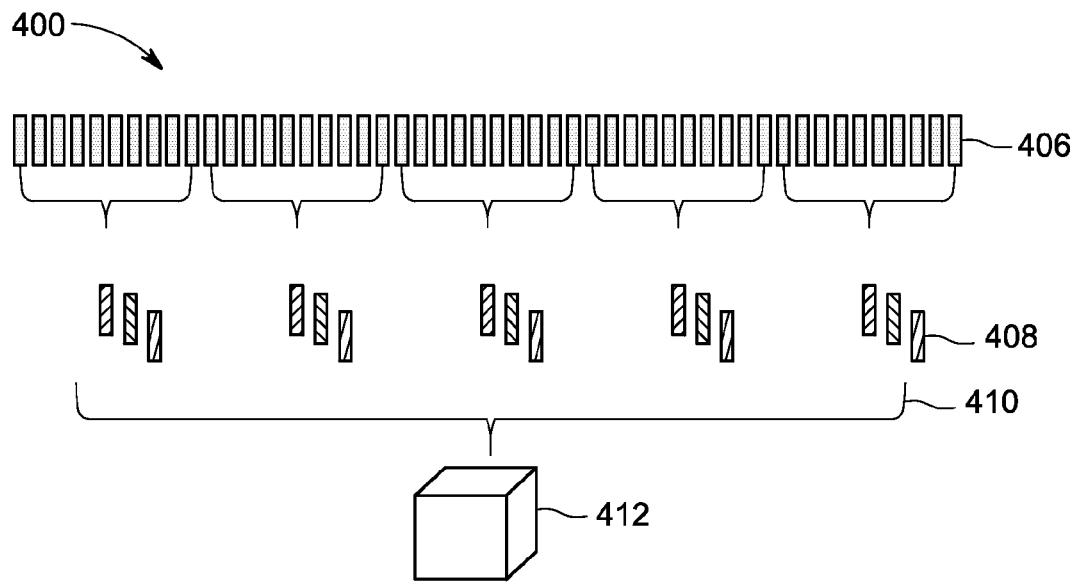
FIGS. 4A and 4B schematically depict data compression processes in accordance with some embodiments.

FIG. 4A schematically depicts data compression process 400 in accordance with some embodiments. The volumetric breast image 412 is obtained from the raw baseline data 406 by use of a grouped data 408. Reconstruction of the volumetric breast image from the raw data can be expressed as equation 1:

$$X = A^{-1} Y \qquad (EQ. 1)$$

where X represents the volumetric breast image 412;

$A^{-1}$ represents the inverse of the forward projection matrix; and

Y represents the raw detector readout data for all projection views 406 (with fine angle sampling).

During 3D reconstruction, the forward projection incorporates the geometry of the system and x-ray physics process for creating charge on the detector after passing through the object. The inverse of the forward projection is not necessarily easy to calculate directly, but iterative and analytic approximations involving the matrix-transpose of the forward projection (called back projection) are successfully used in whole body computerized tomography (CT), breast CT, and DBT.

In accordance with embodiments, data view readouts 406 are grouped into a smaller number of compressed views 408. In the illustrated embodiment, each group of ten raw data view readouts are combined into each of a set of three compressed views, where each respective compressed view is an average formed over the raw data 406 with a specific spatial and temporal resolution. Thus, in this implementation the compression is at a ratio of 10:3.

For example, a pixel value in a compressed view can be the algorithmic mean of the corresponding pixel across ten raw data views. This compressed view has the same spatial resolution of the raw data views. The compressed view's temporal resolution is one-tenth of the raw data and will be subject to motion blur due to tube motion.

Alternately, a compressed view can be a spatially-blurred, down-sampled transform of a single raw data view. In such a case, the compressed view has the same temporal resolution as the raw data view, but with reduced spatial resolution and a fewer number of pixels. The smaller number of pixels relative to the raw data views yields a further data compression ratio. The temporal down-sampling process causes a reduction in the number of bits required to encode the compressed views, but introduces a sampling error and loss of information at neighboring time intervals. In general a pixel in a compressed view will be a combination of spatial blurring and sampling each of the raw data views and then averaging pixels across raw data views.

In a multi-resolution compression, each of the set of the compressed views will be spatially and temporally blurred with different wavelengths or time intervals. In one implementation, a goal could be to retain high spatial frequency information with sparse temporal sampling for some of the compressed views in a set. Also to retain low spatial frequency information with fine temporal sampling for other compressed views in the set.

Reconstruction algorithm 410 preserves the geometry information of the compressed data to reconstruct the approximate three dimensional volume 412 by applying equation 2:

$$X' = f\{A, c_i\} \qquad (EQ. 2)$$

where X' represents the approximate 3D volume 412;

$f\{\ \}$ represents a function of the forward projection matrix A; and $c_i$ represents compressed views of multiple types (e.g., low, high, and/or multiple resolutions).

The function $f\{\ \}$ incorporates the acquired time stamp and spatial sampling corresponding to the compressed views. For example, the function can be implemented by applying the compression process to the forward projection matrix before inversion. In some implementations, iterative solutions and back projection using the transpose of the modified forward projection matrix can be used to solve for the breast volume.

Figure 4B:
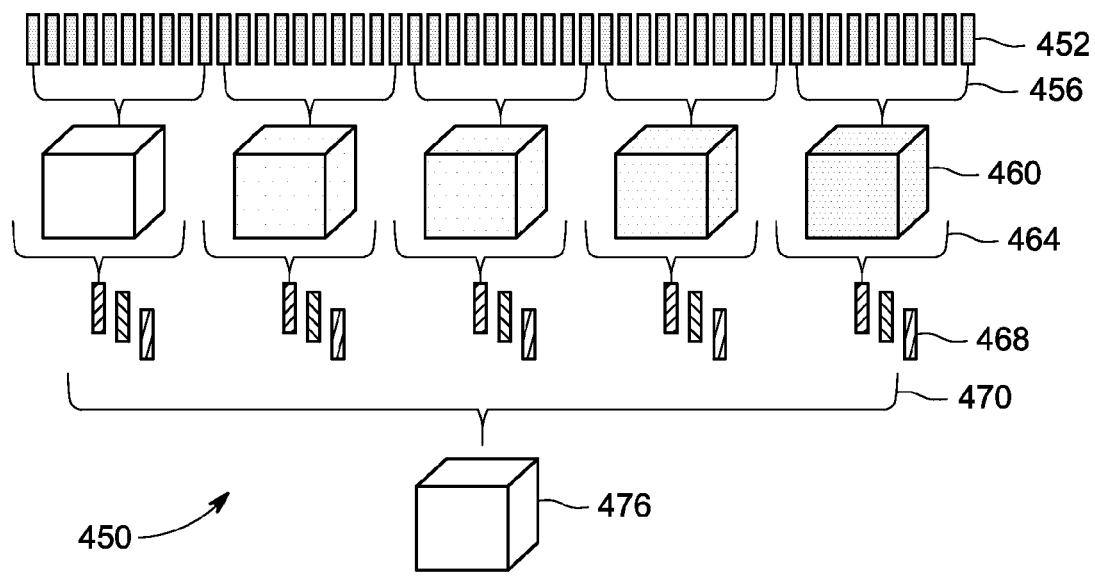

FIG. 4B schematically depicts data compression process 450 in accordance with some embodiments. The reconstruction of the uncompressed baseline data 452 can still be expressed by equation 1. Fast reconstruction process 456 groups the baseline data into the volume domain 460. In one implementation, a filtered back projection (FBP) method can be used. However, other iterative techniques can be equally applied, particularly with small number of iterations on a sparse detector matrix. Each of the intermediate data volumes 460 can be forward projected with a fast operation and compared to the raw data 452. In the interest of compressing the bit storage requirements, the data volume 460 may be highly decimated and spatially coarse relative to the final volume solution 476.

A fast forward projection and difference operator 464 is applied to the volume domain groups 460 to result in compressed views 468, having an overall compression ratio of 10:3. Reconstruction process 470 combines the set of compressed views as in equation 2. In another implementation, compressed views are combined with the intermediate volumes 460 to achieve a best-fit, final three dimensional volume 476 by applying equation 3:

$$X'' = g\{A, v_i, c_i\} \qquad (EQ. 3)$$

where X" is the approximate solution solved using intermediate volumes and compressed views;

A equals the system matrix;

$v_i$ equals accumulating (or independent) volumes;

$c_i$ equals difference projections compared to the original views; and $g\{\ \}$ represents the reconstruction process function.

The primary aspect of a compression process is to reduce the number of bits required to approximate the volume solution X, X', or X". The compression strategy can ensure that the data rate generated by compressed views 408 or 468 can be readily stored on the system and/or transferred by the system to a storage unit with the available bandwidth.

Decimation of data in the detector proceeds by combining pixels values in the same view and in multiple views into an equivalent averaged view. That alternately preserves temporal or spatial information while reducing the bit rate significant factors.

The combination of detector pixels can be performed in a hardware process called "analog binning" or in the digital domain using firmware or software. Otherwise, both lossless and lossy compression algorithms, including the difference from moving average and frequency-based (Huffman coding) can further reduce the number of bits needed on each pixel to specify the detected signal.

A data bit rate reduction can also be implemented by incrementing the voxels in the (volumetric) image domain 460 with weights in accord with the back-projection 456 of the detector values. In this implementation, the compressed views 468 are not retained until the final forward projection operation 464. This has the benefit of reducing the data rate from the detector to the system by storing the data as it is generated in the volume domain where it is finally used and retaining only the error in the compressed views 468.

In accordance with some implementations, the source can be either stationary anode source, or a rotating anode source. The source itself can be a single-spot source, or a multi-spot source—i.e., having an electron gun array that produces a plurality of electron beams, each aimed in a predetermined direction at a respective one of a plurality of targets which receive the electron beams and generate x-rays in response.

In some embodiments, the system controller can relate an angular position of the source to the specific data frame (e.g., global shutter) or detector row readout (rolling shutter). The position of the source may not be exactly reproducible for each acquisition. However, the high data sampling can yield the position information. Real-time position information can be extracted from markers placed in the path of x-rays. The markers are projected to approximately known locations on the detector and the actual position is found in the detected signal. The difference in approximation and actual projected locations can fix the location of the source to a high degree of accuracy for each view, or row-read in the data set. To produce the highest resolution image, the real position of the system components at every point in time can be used in the reconstruction algorithm. The position of system components can be determined by knowing where the pixel is located on the detector, and the location of the source at the time of pixel exposure—via time stamp acquisition. This information can be known by including time stamp data coordinated with the data acquisition.

In accordance with some embodiments, patient motion can be detected in real time during the scan. This follows due to the high temporal sampling of the views. The position of exceptional anatomical features can be tracked by projection onto the detector. Anatomical features of interest include micro-calcifications, fibrous tissues within the breast parenchyma, the edge of the breast skin line, the outline of the pectoral muscle. Such features can be detected by applying image processing segmentation algorithms.

For example, such segmentation may incorporate a priori information about the range of gray-scale values (histogram functional form), and/or the sizes and shape of the objects that serve as useful beacons of patient motion. Once patient motion is detected and the displacement vectors of anatomy are calculated, the results are included in the reconstruction algorithm. By removing these calculated displacement vectors, even clearer images can be produced without anatomical blurring due to patient motion. For example, the raw data can be corrected for the displacement by shifting and non-rigid warping of the pixel matrix. In one implementation if the patient motion exceeds a predetermined threshold, a fault indication can be triggered. The acquisition can then be terminated automatically under system control, or present an operator with the option to terminate the acquisition.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method of synchronizing detector data views and time stamp acquisitions of source angle position, compression of views and transfer of data to a memory location, where subsequent to the acquisition process, the raw and/or compressed data is reconstructed and displayed to the user, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

The invention claimed is:

1. A method of continuous motion digital tomosynthesis, the method comprising:

exposing an object to a programed intensity x-ray beam as an x-ray source travels a pre-determined path, wherein the object is positioned between the x-ray source and a detector, the detector having a plurality of pixels;

accumulating in at least a portion of the plurality of pixels a signal charge from at least a portion of the x-ray beam after the x-ray beam traverses the object;

recording the accumulated signal charge from the plurality of pixels into a digital frame image by reducing a data rate between the plurality of pixels of the detector and the digital frame image by incrementing a quantity of voxels in a volumetric image domain with weights in accord with a back-projection of the digital frame image values, the digital frame image representing raw baseline data;

acquiring information on the source's position and the detector's position when the recording of the plurality of pixels occurs;

compressing the raw baseline data into a plurality of compressed views having a pixel count less than a pixel count of the raw baseline data, where each respective compressed view is an average formed by combining the raw data readouts of the respective compressed view, wherein the combining is performed with at least one of a spatial and a temporal resolution to obtain the compressed view pixel count; and reconstructing a volumetric breast image by processing each respective compressed view with a reconstruction process function that incorporates the acquired position information and a spatial sampling corresponding to the compressed views.

2. The method of claim 1, wherein the programed intensity is a single continuous exposure.

3. The method of claim 1, wherein the reconstruction process function includes applying a compression process to a forward projection matrix before inversion.

4. The method of claim 1, wherein the reconstruction process function includes performing iterative solutions and back projection using a transpose of a modified forward projection matrix.

5. The method of claim 1, wherein the reconstruction process function includes combining respective ones of the compressed views with a respective intermediate volume to achieve a best-fit, final three dimensional volume.

6. The method of claim 1, including decimating the digital frame image by combining pixels values of a same view and in multiple views into an equivalent averaged view.

7. The method of claim 1, including determining patient motion during exposure to the x-ray beam by applying an image processing segmentation process to identify position changes of the patient's anatomical features.

8. A non-transitory computer readable medium having stored thereon instructions which when executed by a processor cause the processor to perform a method of continuous motion tomosynthesis, the method comprising:

exposing an object to a programed intensity x-ray beam as an x-ray source travels a pre-determined path, wherein the object is positioned between the x-ray source and a detector, the detector having a plurality of pixels;

accumulating in at least a portion of the plurality of pixels a signal charge from at least a portion of the x-ray beam after the x-ray beam traverses the object;

recording the accumulated signal charge from the plurality of pixels into a digital frame image by reducing a data rate between the plurality of pixels of the detector and the digital frame image by incrementing a quantity of voxels in a volumetric image domain with weights in accord with a back-projection of the digital frame image values, the digital frame image representing raw baseline data;

acquiring information on the source's position and the detector's position when the recording of the plurality of pixels occurs;

compressing the raw baseline data into a plurality of compressed views having a pixel count less than a pixel count of the raw baseline data, where each respective compressed view is an average formed by combining the raw data readouts of the respective compressed view, wherein the combining is performed with at least one of a spatial and a temporal resolution to obtain the compressed view pixel count; and reconstructing a volumetric breast image by processing each respective compressed view with a reconstruction process function that incorporates the acquired position information and a spatial sampling corresponding to the compressed views.

9. The medium of claim 8, including instructions to cause the processor to control the programed intensity to be a single continuous exposure.

10. The medium of claim 8, including instructions to cause the processor to perform the step of applying a compression process to a forward projection matrix before inversion during the reconstruction process function.

11. The medium of claim 8, including instructions to cause the processor to perform the step of performing iterative solutions and back projection using a transpose of a modified forward projection matrix during the reconstruction process function.

12. The medium of claim 8, including instructions to cause the processor to perform the step of combining respective ones of the compressed views with a respective intermediate volume to achieve a best-fit, final three dimensional volume during the reconstruction process function.

13. The medium of claim 8, including instructions to cause the processor to perform the step of decimating the digital frame image by combining pixels values of a same view and in multiple views into an equivalent averaged view.

14. The medium of claim 8, including instructions to cause the processor to perform the step of determining patient motion during exposure to the x-ray beam by applying an image processing segmentation process to identify position changes of the patient's anatomical features.

15. A continuous motion tomosynthesis apparatus comprising:

a continuous emission x-ray source, the x-ray source configured to travel a pre-determined path;

a detector having a plurality of pixels; and a control processor configured to execute computer-readable instructions that cause the control processor to perform a method including:

exposing an object to a programed intensity x-ray beam as the x-ray source travels a pre-determined path, wherein the object is positioned between the x-ray source and the detector;

accumulating in at least a portion of the plurality of pixels a signal charge from at least a portion of the x-ray beam after the x-ray beam traverses the object;

recording the accumulated signal charge from the plurality of pixels into a digital frame image by reducing a data rate between the plurality of pixels of the detector and the digital frame image by incrementing a quantity of voxels in a volumetric image domain with weights in accord with a back-projection of the digital frame image values, the digital frame image representing raw baseline data;

acquiring information on the source's position and the detector's position when the recording of the plurality of pixels occurs;

compressing the raw baseline data into a plurality of compressed views having a pixel count less than a pixel count of the raw baseline data, where each respective compressed view is an average formed by combining the raw data readouts of the respective compressed view, wherein the combining is performed with at least one of a spatial and a temporal resolution to obtain the compressed view pixel count; and reconstructing a volumetric breast image by processing each respective compressed view with a reconstruction process function that incorporates the acquired position information and a spatial sampling corresponding to the compressed views.

16. The apparatus of claim 15, including instructions to cause the control processor to control the programed intensity to be a single continuous exposure.

17. The apparatus of claim 15, including instructions to cause the control processor during the reconstruction process function to perform one of (1) applying a compression process to a forward projection matrix before inversion, (2) performing iterative solutions and back projection using a transpose of a modified forward projection matrix, and (3) combining respective ones of the compressed views with a respective intermediate volume to achieve a best-fit, final three dimensional volume.

18. The apparatus of claim 15, including instructions to cause the processor to perform the step of decimating the digital frame image by combining pixels values of a same view and in multiple views into an equivalent averaged view.

\* \* \* \* \*